United States Patent
West et al.

(10) Patent No.: US 9,746,451 B2
(45) Date of Patent: Aug. 29, 2017

(54) KINETIC CHLORINE MEASUREMENT

(71) Applicant: Hach Company, Loveland, CO (US)

(72) Inventors: Kevin J. West, Loveland, CO (US);
Brian Harmon, Loveland, CO (US);
Zhao Lu, Fort Collins, CO (US)

( * ) Notice: Subject to any disclaimer, the term of this patent is extended or adjusted under 35 U.S.C. 154(b) by 0 days.

(21) Appl. No.: 14/677,718

(22) Filed: Apr. 2, 2015

(65) Prior Publication Data

US 2015/0285779 A1    Oct. 8, 2015

Related U.S. Application Data

(60) Provisional application No. 61/976,623, filed on Apr. 8, 2014.

(51) Int. Cl.
*G01N 33/18* (2006.01)
*G01N 33/84* (2006.01)

(52) U.S. Cl.
CPC .......... *G01N 33/182* (2013.01); *G01N 33/84* (2013.01)

(58) Field of Classification Search
CPC .................................................. G01N 33/182
See application file for complete search history.

(56) References Cited

U.S. PATENT DOCUMENTS

| | | | |
|---|---|---|---|
| 2003/0077365 A1* | 4/2003 | Howarth ................ | A01N 43/50 426/332 |
| 2009/0320570 A1* | 12/2009 | Wiese .................... | G01N 31/16 73/61.43 |
| 2014/0083865 A1 | 3/2014 | Rowhani et al. | |

OTHER PUBLICATIONS

International Search Report and Written Opinion for PCT/US2015/024119, dated Jul. 24, 2015, 12 pages, European Patent Office, Rijswijk, Netherlands.
International Search Report for PCT/US2015/024119, dated Jul. 24, 2015, 2 pages, European Patent Office, Rijswijk, Netherlands.
Lee et al., "Comparison of colorimetric and membrane introduction mass spectrometry techniques for chloramine analysis", Water Research, vol. 41, No. 14, Jul. 2007, pp. 3097-3102, XP002741457, Elsevier Ltd.
Yun et al., "Modeling of inactivation kinetics of *E-coli* with free chlorine and monochloramine", Database Biosis, Biosciences Information Service, Philadelphia, PA, US, Sep. 2005, Database Accession No. PREV200600093947, 2 pages, XP002741458.

\* cited by examiner

*Primary Examiner* — Paul Hyun
(74) *Attorney, Agent, or Firm* — Ference & Associates, LLC

(57) ABSTRACT

An aspect provides a method of determining a concentration of free chlorine in an aqueous sample, including adding a reagent to the sample, the reagent being reactive with the free chlorine at a first kinetic rate and reactive with at least one chloramine at a second kinetic rate, the first kinetic rate being different from the second kinetic rate; measuring an absorbance response over time resulting from reaction of the free chlorine and the at least one chloramine with the reagent over time; and determining the concentration of the free chlorine in the sample based on a determined rate of change of the absorbance response over time. Other aspects are described and claimed.

22 Claims, 4 Drawing Sheets

KINETIC CHLORINE MEASUREMENT

CLAIM FOR PRIORITY

This application claims the benefit of prior U.S. Provisional Patent Application Ser. No. 61/976,623, entitled "KINETIC CHLORINE MEASUREMENT," filed on Apr. 8, 2014, the contents of which are incorporated by reference in their entirety herein.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosures of all references cited herein are incorporated by reference.

Chlorination of public water supplies has been practiced for almost 100 years in the United States. In that regard, chlorine is an oxidant that kills many harmful microorganisms. Although the pros and cons of disinfection with chlorine have been extensively debated, it remains the most widely used chemical for disinfection of water in the U.S.

Chlorine usually is added to water as the gaseous form or as sodium or calcium hypochlorite. Chlorine gas rapidly hydrolyzes to hypochlorous acid according to the following equation:

$$Cl_2 + H_2O \rightarrow HOCl + H^+ + Cl^-$$

Similarly, aqueous solutions of sodium or calcium hypochlorite will hydrolyze according to:

$$Ca(OCl)_2 + 2H_2O \rightarrow Ca^{2+} + 2HOCl + 2OH^-$$

$$NaOCl + H_2O \rightarrow Na^+ + HOCl + OH^-$$

The two chemical species formed by chlorine in water, hypochlorous acid (HOCl) and hypochlorite ion (OCl$^-$), are commonly referred to as "free available" chlorine. Hypochlorous acid is a weak acid and will disassociate according to:

$$HOCl \leftrightarrow H^+ + OCl^-$$

In waters with pH between 6.5 and 8.5, the reaction is incomplete and both species (HOCl and OCl$^-$) will be present. Hypochlorous acid is the more germicidal of the two.

A relatively strong oxidizing agent, chlorine can react with a wide variety of compounds. Of particular importance in disinfection is the chlorine reaction with nitrogenous compounds, such as ammonia, nitrites and amino acids. Ammonia, commonly present in natural waters, will react with hypochlorous acid or hypochlorite ion to form monochloramine, dichloramine and trichloramine, depending on several factors such as pH and temperature. In breakpoint chlorination, a continual addition of chlorine to the water up to the point where the chlorine requirement is met and all present ammonia is oxidized, so that only free chlorine remains. After the break point, free chlorine (hypochlorous acid plus hypochlorite) is the dominant disinfectant. The free chlorine residual may, for example, be adjusted to maintain a minimum level of 0.2 mg/L Cl$_2$ throughout the distribution system. The importance of break-point chlorination lies in the control of taste and odor and increased germicidal efficiency. The killing power of chlorine in excess of the breakpoint is 25 times higher than that before the breakpoint is reached. Thus, the presence of a free chlorine residual is an indicator of adequate disinfection.

The use of monochloramine as an alternate disinfectant for drinking water has received attention lately as a result of concern about the possible formation of chlorinated by-products when using free chlorine disinfection. However, considerable debate continues regarding the merits of chloramination disinfection.

A standard for free and total chlorine measurement in water is DPD (N,N-diethyl-p-phenylenediamine) colorimetric detection. Total chlorine is the total amount of chlorine in the water including the chlorine that has reacted with nitrogen compounds in the water. In the absence of iodide ion, free chlorine reacts quickly with DPD indicator to produce a red color, whereas chloramines react more slowly. If a small amount of iodide ion is added, chloramines also react to produce color, yielding total chlorine concentration. Absorbance (for example, at 515 nm) may be spectrophotometrically measured and compared to a series of standards, using a graph or a regression analysis calculation to determine free and/or total chlorine concentration.

As set forth above, free chlorine reacts very quickly with DPD while the chloramine species (for example, monochloramine and dichloramine) react more slowly. In attempting to measure free chlorine, the presence of "interfering" species such as monochloramine may produce inaccurate readings. For greatest accuracy, it is typically recommended that the free chlorine measurement using DPD should be made quickly (that is, before the interfering species can react to any significant degree).

Alternatively, additional reagents may be added to prevent reaction of interfering species, pre-determine the amounts of interfering species, or post-determine the amounts of interfering species. For example, sodium arsenite or thioacetamide can be used to reduce the effects of or prevent interference by monochloramine. However, such additional reagents can be toxic and/or expensive.

Current methods, systems and kits for free chlorine measurement using the DPD colorimetric test are limited because the presence of chloramines can introduce significant errors in free chlorine measurements. Once again, if additional reagents are used to prevent interferences, then additional steps and/or toxic and expensive chemicals are required. Further, the traditional DPD colorimetric test does not allow monochloramine concentration to be measured directly.

BRIEF SUMMARY

In summary, one aspect provides a method of determining a concentration of free chlorine in an aqueous sample, comprising: adding a reagent to the sample, the reagent being reactive with the free chlorine at a first kinetic rate and reactive with at least one chloramine at a second kinetic rate, the first kinetic rate being different from the second kinetic rate; measuring an absorbance response in the sample over time resulting from reaction of the free chlorine and the at least one chloramine with the reagent over time; and determining the concentration of the free chlorine in the sample based on a determined rate of change of the absorbance response over time.

Another aspect provides a system of determining a concentration of free chlorine in an aqueous solution, comprising: a measuring system that measures an absorbance response over time resulting from reaction of the free chlorine and at least one chloramine with a reagent over time after the reagent is added to the solution, the reagent being reactive with the free chlorine at a first kinetic rate and reactive with the at least one chloramine at a second kinetic rate, the first kinetic rate being different from the second kinetic rate; and a processor system adapted to determine the concentration of the free chlorine in the solution based on a determined rate of change of the response over time.

A further aspect provides a kit comprising: a reagent system comprising at least one of DPD (N,N-diethyl-p-phenylenediamine) and SBT (N,N'-bis(2,4-di-sulfobenzyl) tolidine tetrasodium salt); a measuring system that measures an absorbance response over time resulting from reaction of the free chlorine and at least one chloramine with a reagent over time, the reagent being reactive with the free chlorine at a first kinetic rate and reactive with the at least one chloramine at a second kinetic rate, the first kinetic rate being different from the second kinetic rate; and a processor system adapted to determine the concentration of the free chlorine in the sample based on a determined rate of change of the measured absorbance response over time.

The present devices, systems, methods and kits, along with the attributes and attendant advantages thereof, will best be appreciated and understood in view of the following detailed description taken in conjunction with the accompanying drawings.

DETAILED DESCRIPTION

Figure 1:
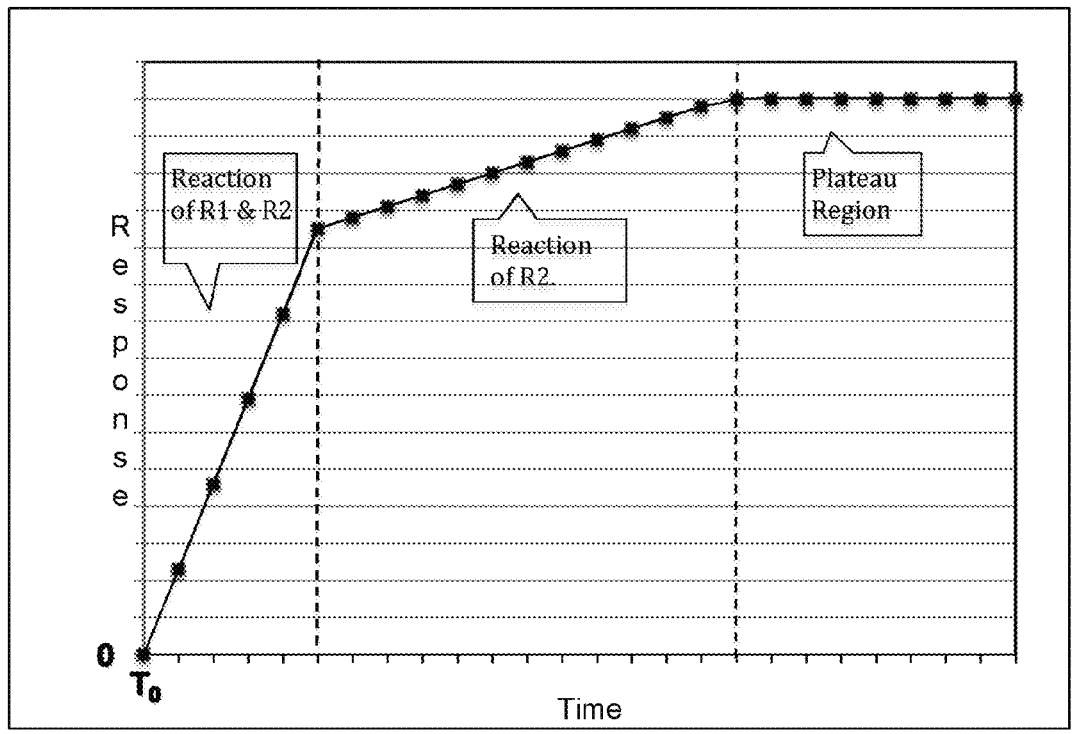
FIG. 1 illustrates a response curve showing simultaneous reaction of a fast reacting analyte and a slower reacting interfering species with a reagent as a function of time.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a reagent" includes a plurality of such reagents and equivalents thereof known to those skilled in the art, and so forth, and reference to "the reagent" is a reference to one or more such reagents and equivalents thereof known to those skilled in the art, and so forth. Recitation of ranges of values herein are merely intended to serve as a shorthand method of referring individually to each separate value falling within the range. Unless otherwise indicated herein, and each separate value as well as intermediate ranges are incorporated into the specification as if individually recited herein. All methods described herein can be performed in any suitable order unless otherwise indicated herein or otherwise clearly contraindicated by the text.

Quantifying the amount or concentration of an analyte is a common laboratory and field method. In many methods, a reagent or reagent system (usually added stoichiometrically or in excess) reacts with the analyte to determine concentration. By measuring a specific outcome of the reaction, the analyte concentration can be deduced. There are many types of reactions and also many ways of measuring reaction between reagent and analyte. A measured response may, for example, include a colorimetric change, a pH change, a temperature change, an electrical property change, a spectrophotometric change, or precipitation.

Quantification of analytes often has complications. For example, the analyte to be quantified often exists in solution/mixture with other compounds that interfere with the analysis. Additionally, time, temperature, pressure, or other physical parameters can cause complications. Interference is created when one or more species, in addition to the analyte, is/are present that react with the reagent in a manner to effect the measure response. In such situations, it can be very difficult or even impossible to accurately determine the concentration of the primary analyte. As described above, chloramines such as monochloramine act as interference when measuring free chlorine in DPD colorimetric detection. Similar interferant problems arise using the reagent SBT (N,N'-bis(2,4-di-sulfobenzyl)tolidine tetrasodium salt) for measuring free chlorine. DPD, SBT and any salt thereof may, for example, be used as reagents herein.

A common way of removing these interferences is by physically treating the analyte solution/mixture to purify it, and/or create conditions more suited for the analysis. For example, interfering analytes can sometimes be removed via distillation or selective reaction with a second reagent. In addition, temperature can often be used to negate time complications. These methods normally increase time and cost of the method, introduce complexities, or introduce toxic and/or expensive chemicals. In the case of DPD and SBT colorimetric detection, for example, sodium arsenite or thioacetamide may be added to reduce the effects of or prevent interference by monochloramine, but give rise to increased time, expense and toxicity.

It has been found when two or more reactants (for example, a target analyte and one or more interferants) are present in a mixture or solution that react with the reagent in a similar way (that is, contributing to the response to be measured), and their respective rates of reaction with the reagent are different, by measuring the response (extent of reaction) over time, the concentration(s) of the analyte reactant as well as the other reactants can be quantitatively determined without physically treating the analyte solution. It has also been found, that this method of analysis can result in better accuracy and precision compared to standard methods of analysis.

In general, a concentration of at least a first chemical species (for example, free chlorine) in a mixture including the first chemical species and at least a second chemical species (for example, monochloramine) may be determined by adding a reagent to the mixture. The reagent is reactive with the first chemical species at a first kinetic rate and reactive with the second chemical species at a second kinetic rate, wherein the first kinetic rate is different from the second kinetic rate. The response resulting from reaction of the first chemical species and the second chemical species with the reagent is measured over time, and the concentration of the first chemical species in the mixture is determined based on a determined rate of change of the response over time.

In the case that the first kinetic rate is faster than the second kinetic rate, the rate of change of the response may be determined during a time period wherein substantially all of the first chemical species has reacted with the reagent. In the case of the measurement of free chlorine, such a time period may, for example, occur in the range of 5 seconds to two minutes (or, for example, 30 seconds to one minute) after a time $T_0$ which corresponds to a time after the reagent (for example, DPD or SBT) is added to the mixture. In a number of embodiments, the time period for measurement was centered around 45 seconds after $T_0$. In a number of embodiments, the rate of change of the response during the time period is used to determine a response at a time $T_0$, from which the concentration of the first chemical species is determined. By modeling or extrapolating, to determine the response at $T_0$, the value of the response obtained at the $T_0$-intercept corresponds to the concentration of first chemical species (having the faster kinetic rate). Once the concentration of the first chemical species is determined, the concentration of the second, more slowly reacting chemical species (for example, monochloramine) can be determined from the response.

Alternatively or additionally, the rate of change of the response during the time period may be used to determine a correction factor related to the concentration of the second chemical species, and the concentration of the first chemical species may be determined using the correction factor. The correction factor may, for example, correspond to the contribution of the second chemical species to the measured response, and the contribution of the second chemical species may be determined from a model which may, for example, be experimentally determined. For example, the model may provide the contribution or the concentration of the second chemical species as a function of the rate of change of the response during the time period. Temperature and reagent quantity may also be incorporated into the model.

The rate equation for reaction between an analyte or first chemical species R1 and reagent to form a product, P, can be expressed as $$r_p = k[R1]^x[\text{reagent}]^y \quad \text{(Eqn. 1)}$$

where $r_p$ is the rate of reaction, [R1] and [reagent] are concentrations of R1 and the reagent in solution, k is the rate constant which is a function of temperature and other reaction variables, and x and y are the orders of reaction for R1 and the reagent, respectively. For reactions where reagent is added in excess and the rate constant is constant, the rate of reaction varies mainly with R1 concentration.

In a simple embodiment where two reactants are present, R1 and a second chemical species or interferant R2, that both react with reagent to form product, P, the kinetic expression can be expressed as $$r_p = k_1[R1]^{x1}[\text{reagent}]^{y1} + k_2[R2]^{x2}[\text{reagent}]^{y2} \quad \text{(Eqn. 2)}$$

where $r_p$ is the rate of reaction, [R1], [R2] and [reagent] are concentrations of the first chemical species, the second chemical species, and reagent in solution, $k_1$ and $k_2$ are the rate constants (which are functions of temperature and other variables), x1 and y1 are the orders of reaction for reaction of R1 with reagent respectively, and x2 and y2 are the orders of reaction for reaction of R2 and reagent respectively.

In the representative example wherein R1 (free chlorine) reacts with the reagent (DPD), but R1 reacts quicker than R2 (monochloramine), the extent of reaction can be plotted as a response curve as illustrated in an idealized manner in FIG. 1, wherein the measured response (for example, absorbance) corresponds to and can quantify the extent of reaction. The response curve of FIG. 1 can be divided into three sections or time periods. In a first section, between time $T_0$ and the first dashed line of FIG. 1, the measured response corresponds to the reaction of both R1 and R2. In the second section or time period between the first and second dashed lines of FIG. 1, the measured response corresponds to the reaction of only R2 as substantially all of R1 (the species with the faster kinetic rate) has reacted. In the third section, to the right of the second dashed line in FIG. 1, a plateau region is reached, indicating completion of the reaction of R2 with the reagent. The slope of the response curve at any point in time corresponds to overall rate of reaction at that time.

As discussed below in the representative examples for free chlorine and monochloramine, the response/reaction rate during the time period when the response corresponds to the reaction of monochloramine only can be used to determine the concentration of free chlorine as well as the concentration of monochloramine with increased accuracy as compared to previous methods. The methods hereof for determining two analyte concentrations can be extended to three or more analytes, when the response curves can be separated into distinct portions as described above.

As described above, the standard for chlorine measurement in water is DPD (N,N-diethyl-p-phenylenediamine) colorimetric detection. Alternatively, N,N'-bis(2,4-di-sulfobenzyl)tolidine tetrasodium salt (SBT) can be used as a chromogenic indicator for oxidizing substances, and has been shown to be a good indicator for chlorine in water. Once again, free chlorine reacts very quickly with DPD while other chlorine containing species such as chloramines react more slowly. Assuming rapid mixing, when the DPD indicator is added to a free chlorine containing water sample, color change is almost instantaneous. In currently practiced methods, the initial color change is used to calculate free chlorine concentration.

Monochloramine can, for example, cause a 2.6 to 6.0% interference/error in free chlorine measurement depending on monochloramine concentration, temperature, mixing, and time factors. Monochloramine causes a gradual drift in absorbance measurement to higher readings. Thus, to minimize chloramine interference, the free chlorine measurement under current practice must be made as quickly as possible. However, it can be challenging to make the free chlorine reading before chloramine causes a significant error. To overcome the shortcomings of the DPD colorimetric test for free Cl determination, the rate of change of the measured DPD colorimetric response over time was investigated.

In a number of studies, samples including free chlorine in water with varying amount of monochloramine were prepared. Free chlorine was prepared as a dilute bleach solution. A solution of monochloramine was prepared by mixing 0.1 mL of an available ammonium chloride solution (0.153 g/mL) and 0.5 mL pH 8.3 buffer with 100 mL distilled water. A 0.5 mL aliquot of commercial bleach was then added slowly while stirring the solution. The DPD reagent used was available from Hach Company of Loveland, Colo. (HACH® Free Chlorine Test Kit (Cat No. 21055-69)). Solution volumes were measured using TenSette® pipets and micropipettes. Chlorine concentrations were determined using a HACH DR3800™ benchtop spectrometer (Model LPG424.99.0002).

Two sets of studies were performed. The samples for each study set were prepared in a similar manner. A 10 mL aliquot of distilled water was placed into a 1-inch square sample cell. A fixed volume of free chlorine was added, followed by a variable volume of monochloramine solution. Set 1 used a constant free chlorine solution volume of 0.100 mL while the monochloramine solution volume was varied from 0.000 mL added to 0.100 mL added in 0.020 mL steps for a total of six sample solutions. Set 2 used a constant free chlorine solution volume of 0.050 mL for six samples while the monochloramine solution volume was varied in the same manner as in Set 1. The Set 2 studies also included a seventh sample that contained no added free chlorine and 0.100 mL of the monochloramine solution. The sample cell was swirled to mix the solutions and one free chlorine powder pillow was added. After rapidly mixing the DPD reagent with the sample, a timer was started, the sample cell was placed in the spectrophotometer, and an initial chlorine concentration acquired. Additional chlorine concentrations were acquired at the one-minute mark, two-minute mark, and three-minute mark after the addition of the DPD reagent.

Figure 2:
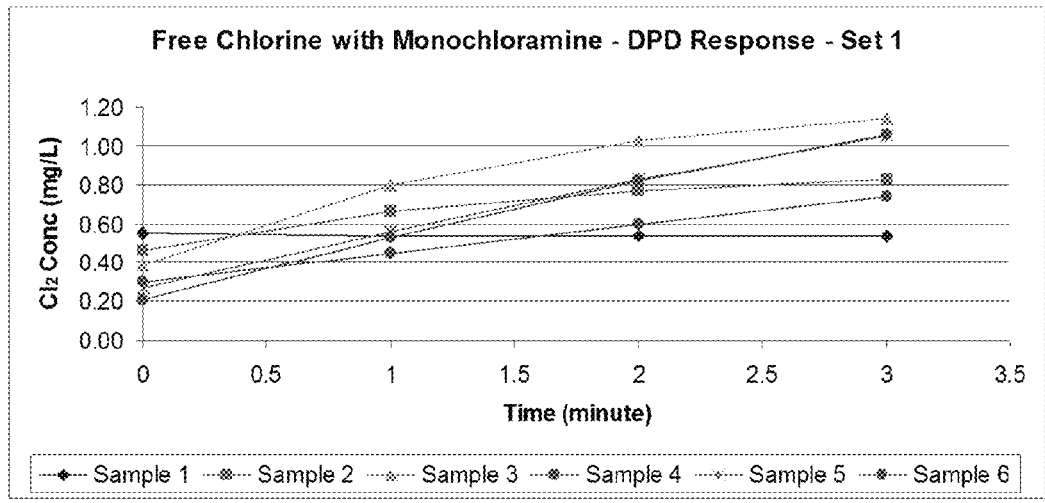
FIG. 2 illustrates measured chlorine concentrations as a function of time for solutions of free chlorine with monochloramine for a first set of studies.
Figure 3:
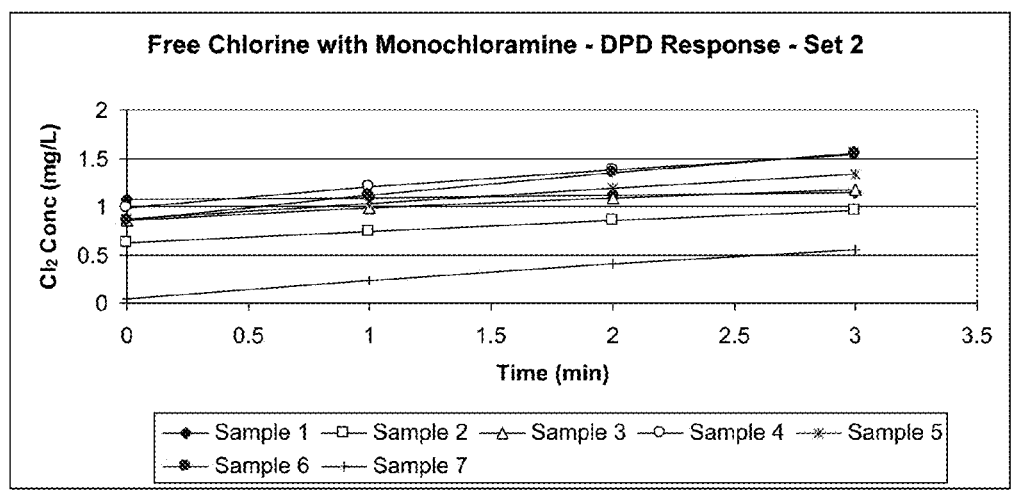
FIG. 3 illustrates measured chlorine concentrations as a function of time for solutions of free chlorine with monochloramine for a second set of studies.

Table 1 and FIG. 2 set forth data of measured free chlorine concentration measured at 0 minutes, 1 minute, 2 minutes, and 3 minutes (from $T_0$) collected for the studies of Set 1, while Table 2 and FIG. 3 set forth similar data collected for the studies of Set 2.

TABLE 1

Chlorine concentrations (mg/L $Cl_2$) measured in Set 1.

| Sample | 0 Minute | 1 Minute | 2 Minute | 3 Minute |
|---|---|---|---|---|
| 1 | 0.55 | 0.54 | 0.54 | 0.54 |
| 2 | 0.46 | 0.66 | 0.77 | 0.83 |
| 3 | 0.39 | 0.80 | 1.03 | 1.14 |
| 4 | 0.30 | 0.45 | 0.60 | 0.74 |
| 5 | 0.27 | 0.56 | 0.83 | 1.05 |
| 6 | 0.21 | 0.53 | 0.82 | 1.06 |

TABLE 2

Chlorine concentrations (mg/L $Cl_2$) measured in Set 2.

| Sample | 0 Minute | 1 Minute | 2 Minute | 3 Minute |
|---|---|---|---|---|
| 1 | 1.07 | 1.09 | 1.12 | 1.14 |
| 2 | 0.62 | 0.74 | 0.85 | 0.96 |
| 3 | 0.86 | 0.98 | 1.08 | 1.18 |
| 4 | 0.98 | 1.21 | 1.38 | 1.53 |
| 5 | 0.87 | 1.03 | 1.19 | 1.33 |
| 6 | 0.86 | 1.12 | 1.35 | 1.55 |
| 7 | 0.04 | 0.23 | 0.40 | 0.55 |

Three different calculations were performed to obtain a "calculated" free chlorine concentration determined as an intercept value for the concentration at time zero. In the studies hereof, all three calculations used only the concentration values obtained at times 1 minute and 2 minutes. Calculation A used the "Intercept" function available in MICROSOFT EXCEL® to calculate the intercept of a linear least squares line. Calculation B used equation 3 below to calculate a value at time 0.

ResponseMinute 0=ResponseMinute 1−(ResponseMinute 2−ResponseMinute 1)  (Eqn. 3)

Calculation C was a rearrangement of equation 3, used for Calculation B, to arrive at an equation 4 that was easier to calculate as follows:

ResponseMinute 0=(2×ResponseMinute 1)−ResponseMinute 2.  (Eqn. 4)

The results of each calculation method along with the difference from the measured $T_0$ concentration are set forth in Table 3.

TABLE 3

Calculated chlorine concentrations (mg/L $Cl_2$) and difference.

| Set 1 | Sample 1 | Sample 2 | Sample 3 | Sample 4 | Sample 5 | Sample 6 |
|---|---|---|---|---|---|---|
| Measured | 0.055 | 0.46 | 0.39 | 0.30 | 0.27 | 0.21 |
| A | 0.54 | 0.55 | 0.57 | 0.30 | 0.29 | 0.24 |
| B | 0.54 | 0.55 | 0.57 | 0.30 | 0.29 | 0.24 |
| C | 0.54 | 0.55 | 0.57 | 0.30 | 0.29 | 0.24 |
| Difference | −0.01 | 0.09 | 0.18 | 0.00 | 0.02 | 0.03 |

TABLE 3-continued

Calculated chlorine concentrations (mg/L $Cl_2$) and difference.

| Set 2 | Sample 1 | Sample 2 | Sample 3 | Sample 4 | Sample 5 | Sample 6 | Sample 7 |
|---|---|---|---|---|---|---|---|
| Measured | 1.07 | 0.62 | 0.86 | 0.98 | 0.87 | 0.86 | 0.04 |
| A | 1.06 | 0.63 | 0.88 | 1.04 | 0.87 | 0.89 | 0.06 |
| B | 1.06 | 0.63 | 0.88 | 1.04 | 0.87 | 0.89 | 0.06 |
| C | 1.06 | 0.63 | 0.88 | 1.04 | 0.87 | 0.89 | 0.06 |
| Difference | −0.01 | 0.01 | 0.02 | 0.06 | 0.00 | 0.03 | 0.02 |

All three calculation methods resulted in substantially the same values for the intercept. The calculation C method was arguably the easiest to perform. Most of the sample solutions had calculated free chlorine concentration values that were very near the measured chlorine concentration values. There are three sample solutions that had relatively large differences: Samples 2 and 3 of Set 1, and Sample 4 of Set 2. During the data collection for Set 2 Sample 4, for example, it is known that problems were encountered in starting the timer. Since this approach relies on the slower reaction rate of monochloramine with DPD, time is an important parameter. Based on the data collected in these studies, this approach was found to be an alternative method of compensating for the monochloramine reaction during determination of free chlorine with DPD.

To explore this approach further, a temperature evaluation and a more extensive concentration evaluation relating to the DPD colorimetric method for measuring chlorine in water were undertaken. In a number of studies of temperature effect, stock solutions of free chlorine and monochloramine were placed into a constant temperature water bath. A bottle containing approximately 100 mL of distilled water was also placed into the same water bath. The water bath was set to a temperature of 15° C. and a one-hour time period was allowed for the contents to come to temperature. A series of seven sample solutions were prepared in a manner similar to that reported above. Once prepared, sample temperature was not controlled during the measurement time period. This procedure mimics the measurement process performed in the field. The chlorine concentration was recorded at time intervals of 0 minutes (<10 seconds after DPD addition), 1 minute, 2 minutes, and 3 minutes after reagent addition ($T_0$). Once the series of samples had been measured, the water bath temperature was changed to 25° C. and the measurement procedure was repeated. The temperature of the water bath was then set to 35° C. for one additional measurement cycle.

Studies of expanded concentration response were performed in a manner similar to the initial studies with the added variation of the free chlorine concentration. The volume of the free chlorine stock solution added to each sample was varied from 0.000 mL to 0.100 mL in 0.020 mL steps. The volume of monochloramine stock solution added was varied in the same manner. A total of 36 sample solutions were prepared. The concentration values obtained were manually recorded at 0 minute, 1 minute, and 2 minute intervals only.

Data for the temperature evaluation studies are set forth in Table 4. Data for the expanded concentration response studies are presented in Table 5.

TABLE 4

Chlorine concentration data obtained at selected temperatures.

| Minute | Sample 1 | Sample 2 | Sample 3 | Sample 4 | Sample 5 | Sample 6 | Sample 7 |
|---|---|---|---|---|---|---|---|
| Temperature = 15° C. | | | | | | | |
| 0 | 0.91 | 0.82 | 0.71 | 0.59 | 0.51 | 0.43 | 0.03 |
| 1 | 0.88 | 0.83 | 0.75 | 0.65 | 0.60 | 0.55 | 0.09 |
| 2 | 0.89 | 0.86 | 0.80 | 0.73 | 0.70 | 0.70 | 0.18 |
| 3 | 0.90 | 0.89 | 0.85 | 0.80 | 0.79 | 0.84 | 0.26 |
| Temperature = 25° C. | | | | | | | |
| 0 | 0.94 | 0.74 | 0.69 | 0.58 | 0.49 | 0.42 | 0.03 |
| 1 | 0.93 | 0.77 | 0.73 | 0.66 | 0.61 | 0.56 | 0.13 |
| 2 | 0.94 | 0.80 | 0.78 | 0.76 | 0.74 | 0.73 | 0.24 |
| 3 | 0.93 | 0.83 | 0.83 | 0.85 | 0.85 | 0.88 | 0.34 |
| Temperature = 35° C. | | | | | | | |
| 0 | 0.98 | 0.88 | 0.71 | 0.59 | 0.50 | 0.40 | 0.05 |
| 1 | 0.98 | 0.92 | 0.79 | 0.74 | 0.65 | 0.59 | 0.23 |
| 2 | 0.98 | 0.96 | 0.87 | 0.87 | 0.81 | 0.79 | 0.41 |
| 3 | 0.98 | 0.99 | 0.94 | 0.99 | 0.95 | 0.96 | 0.57 |

Note:
The values in the table are concentrations as mg/L $Cl_2$.

TABLE 5

Concentration values obtained with variable free chlorine and monochloramine.

| Volume Monochloramine Added | Minute | \multicolumn{6}{c}{Volume Free Chlorine Added} |
|---|---|---|---|---|---|---|---|

| Volume Monochloramine Added | Minute | 0.00 mL | 0.02 mL | 0.04 mL | 0.06 mL | 0.08 mL | 0.10 mL |
|---|---|---|---|---|---|---|---|
| 0.00 mL | 0 | 0.01 | 0.38 | 0.73 | 1.09 | 1.40 | 1.75 |
|  | 1 | 0.00 | 0.37 | 0.72 | 1.08 | 1.39 | 1.75 |
|  | 2 | 0.00 | 0.37 | 0.72 | 1.08 | 1.40 | 1.75 |
| 0.02 mL | 0 | 0.02 | 0.27 | 0.57 | 0.95 | 1.27 | 1.60 |
|  | 1 | 0.02 | 0.29 | 0.59 | 0.97 | 1.29 | 1.61 |
|  | 2 | 0.04 | 0.33 | 0.62 | 1.01 | 1.32 | 1.64 |
| 0.04 mL | 0 | 0.02 | 0.21 | 0.52 | 0.84 | 1.20 | 1.53 |
|  | 1 | 0.03 | 0.24 | 0.56 | 0.88 | 1.23 | 1.56 |
|  | 2 | 0.07 | 0.30 | 0.61 | 0.93 | 1.28 | 1.60 |
| 0.06 mL | 0 | 0.04 | 0.19 | 0.40 | 0.75 | 1.09 | 1.38 |
|  | 1 | 0.07 | 0.25 | 0.47 | 0.83 | 1.15 | 1.43 |
|  | 2 | 0.14 | 0.33 | 0.56 | 0.93 | 1.23 | 1.51 |
| 0.08 mL | 0 | 0.04 | 0.11 | 0.32 | 0.63 | 0.99 | 1.43 |
|  | 1 | 0.09 | 0.19 | 0.40 | 0.72 | 1.06 | 1.50 |
|  | 2 | 0.16 | 0.29 | 0.50 | 0.83 | 1.16 | 1.60 |
| 0.10 mL | 0 | 0.04 | 0.09 | 0.26 | 0.57 | 0.87 | 1.25 |
|  | 1 | 0.12 | 0.20 | 0.35 | 0.67 | 0.94 | 1.36 |
|  | 2 | 0.23 | 0.34 | 0.48 | 0.81 | 1.05 | 1.49 |

Note:
The values in the table are concentrations as mg/L $Cl_2$.

Chlorine concentrations at minute zero ($T_0$) were calculated using Equation 4 as set forth above. The calculated minute zero concentrations along with the measured minute zero concentrations and calculated difference between the two are given in Table 6 for the temperature studies and Table 7 for the variable free chlorine and monochloramine studies.

TABLE 6

Calculated free chlorine concentration and difference for temperature evaluation.

Temperature = 15° C.

|  | Sample 1 | Sample 2 | Sample 3 | Sample 4 | Sample 5 | Sample 6 | Sample 7 |
|---|---|---|---|---|---|---|---|
| Minute 0 | 0.91 | 0.82 | 0.71 | 0.59 | 0.51 | 0.43 | 0.03 |
| Calculated | 0.87 | 0.80 | 0.70 | 0.57 | 0.50 | 0.40 | 0.00 |
| Difference | −0.04 | −0.02 | −0.01 | −0.02 | −0.01 | −0.03 | −0.03 |

Temperature = 25° C.

| Minute | Sample 1 | Sample 2 | Sample 3 | Sample 4 | Sample 5 | Sample 6 | Sample 7 |
|---|---|---|---|---|---|---|---|
| Minute 0 | 0.94 | 0.74 | 0.69 | 0.58 | 0.49 | 0.42 | 0.03 |
| Calculated | 0.92 | 0.74 | 0.68 | 0.56 | 0.48 | 0.39 | 0.02 |
| Difference | −0.02 | 0.00 | −0.01 | −0.02 | −0.01 | −0.03 | −0.01 |

Temperature = 35° C.

| Minute | Sample 1 | Sample 2 | Sample 3 | Sample 4 | Sample 5 | Sample 6 | Sample 7 |
|---|---|---|---|---|---|---|---|
| Minute 0 | 0.98 | 0.88 | 0.71 | 0.59 | 0.50 | 0.40 | 0.05 |
| Calculated | 0.98 | 0.88 | 0.71 | 0.61 | 0.49 | 0.39 | 0.05 |
| Difference | 0.00 | 0.00 | 0.00 | 0.02 | −0.01 | −0.01 | 0.00 |

Note:
The values in the table are concentrations as mg/L $Cl_2$.

TABLE 7

Calculated free chlorine concentration and difference for variable volume evaluation.

| Volume Monochloramine Added |  | 0.00 mL | 0.02 mL | 0.04 mL | 0.06 mL | 0.08 mL | 0.10 mL |
|---|---|---|---|---|---|---|---|
| 0.00 mL | Min 0 | 0.01 | 0.38 | 0.73 | 1.09 | 1.40 | 1.75 |
|  | Calc'd | 0.00 | 0.37 | 0.72 | 1.08 | 1.38 | 1.75 |
|  | Diff. | −0.01 | −0.01 | −0.01 | −0.01 | −0.02 | 0.00 |
| 0.02 mL | Min 0 | 0.02 | 0.27 | 0.57 | 0.95 | 1.27 | 1.60 |
|  | Calc'd | 0.00 | 0.25 | 0.56 | 0.93 | 1.26 | 1.58 |
|  | Diff. | −0.02 | −0.02 | −0.01 | −0.02 | −0.01 | −0.02 |
| 0.04 mL | Min 0 | 0.02 | 0.21 | 0.52 | 0.84 | 1.20 | 1.53 |
|  | Calc'd | −0.01 | 0.18 | 0.51 | 0.83 | 1.18 | 1.52 |
|  | Diff. | −0.03 | −0.03 | −0.01 | −0.01 | −0.02 | −0.01 |
| 0.06 mL | Min 0 | 0.04 | 0.19 | 0.40 | 0.75 | 1.09 | 1.38 |
|  | Calc'd | 0.00 | 0.17 | 0.38 | 0.73 | 1.07 | 1.35 |
|  | Diff. | −0.04 | −0.02 | −0.02 | −0.02 | −0.02 | −0.03 |
| 0.08 mL | Min 0 | 0.04 | 0.11 | 0.32 | 0.63 | 0.99 | 1.43 |
|  | Calc'd | 0.02 | 0.09 | 0.30 | 0.61 | 0.96 | 1.40 |
|  | Diff. | −0.02 | −0.02 | −0.02 | −0.02 | −0.03 | −0.03 |
| 0.10 mL | Min 0 | 0.04 | 0.09 | 0.26 | 0.57 | 0.87 | 1.25 |
|  | Calc'd | 0.01 | 0.06 | 0.22 | 0.53 | 0.83 | 1.23 |
|  | Diff. | −0.03 | −0.03 | −0.04 | −0.04 | −0.04 | −0.02 |

Note:
The values in the table are concentrations as mg/L $Cl_2$.

The calculated chlorine concentrations in Table 6 reveal that sample temperature (between 15 and 35° C.) at the beginning of the evaluation did not have an effect on the values obtained. All of the calculated chlorine concentrations differed by less than 0.05 mg/L $Cl_2$ compared to the concentration values measured at time zero. Many of the calculated concentration values were less than the concentration value obtained at time 0. This was a result of some monochloramine reacting in the short time period from when the DPD reagent was added until the measurement was made. An attempt was made to keep this time interval less than 10 seconds. However, it is possible that some monochloramine had reacted during this short interval. There may also be some variation with the initial sample temperature but this variation was small compared to the temperature range evaluated.

The calculated chlorine concentrations in Table 7 suggest that the magnitude of the free chlorine and monochloramine present do not alter the determined differences seen with previous studies (in which only the quantity of monochloramine present was varied with a constant free chlorine concentration). Again, the differences obtained between the calculated chlorine concentrations and the measured chlorine concentrations at time zero were small with the calculated values being lower than the measured values.

The above method of measuring free chlorine in the presence of monochloramine works for samples at typical temperatures and free chlorine concentrations across the method concentration range. The one-minute interval was initially selected as being a convenient time interval to wait after the addition of the DPD reagent and between the measurements. However, it may be possible to use a shorter time interval, such as 30 seconds, so that the entire measurement is completed in one minute rather than two minutes as set forth above.

Another reaction kinetics methodology for measurement of free chlorine in the presence of chloramines (for example, including monochloramine) with a reagent such as DPD at various temperatures is discussed below. In that regard, reaction kinetics (temperature and concentration) of free chlorine and monochloramine were used to develop a method to correct for monochloramine interference during free chlorine measurement using, for example, the DPD colorimetric method.

Monochloramine standards were made, including 0, 0.25, 1, 2, 3, and 4 mg/L. The pH of the samples ranged between 9.0-9.22. Standards were independently verified using a HACH brand DR6000 spectrophotometer available from Hach Company, Loveland, Colo. In measurements using the instrument, 8 repetitions were performed for each standard sample. For each $NH_2Cl$ standard, the temperature was set to 5, 10, 20, 30, 40 and 50° C.

Figure 4:
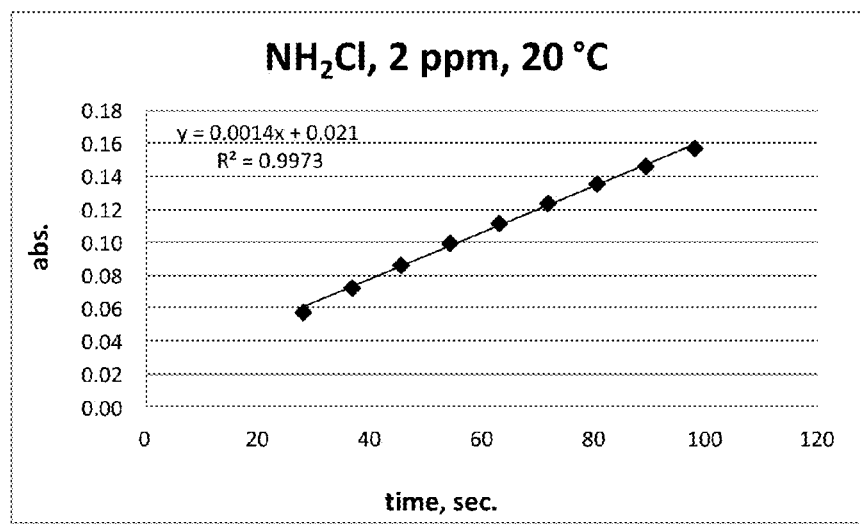
FIG. 4 illustrates the reaction profile (absorbance vs. time) for reaction of DPD with 2 ppm monochloramine standards (at 20° C.).

Absorbance at different reaction times was recorded at all monochloramine concentrations and at all the studied temperatures, but only the 2 ppm and 20° C. data is shown in FIG. 4, i.e., a plot of absorbance as a function of time.

Figure 5:
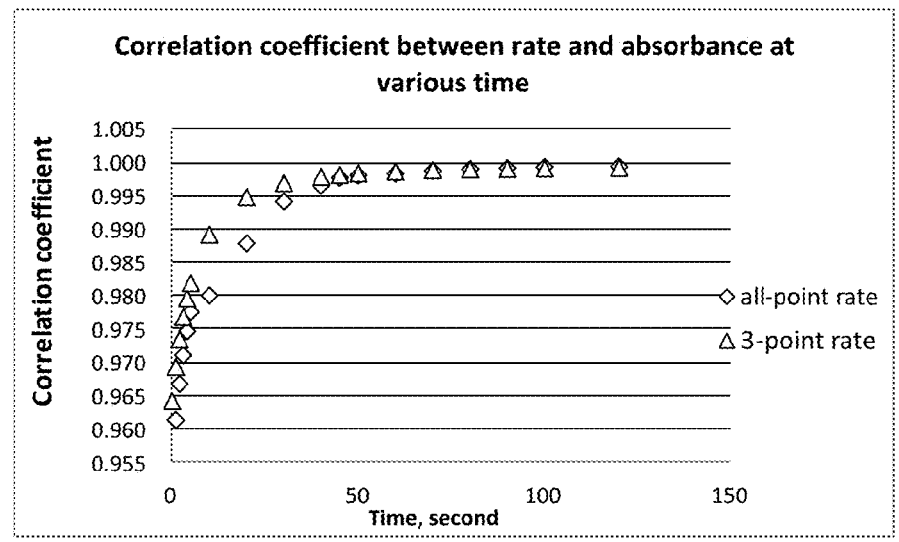
FIG. 5 illustrates correlation coefficients (between absorbance and reaction rate) for reaction of DPD with a solution of free chlorine with monochloramine as a function of time at 20° C., wherein two calculated reaction rates are shown (the first using all the data, and the second using 3 data points close to 45 seconds).

The reaction rate can, for example, be calculated using a linear or polynomial curve fit of the reaction profile, absorbance vs. reaction time. In a number of studies, a linear curve fit was used to derive reaction rate from the absorbance vs. reaction time data. Absorbance at different reaction times was correlated to the calculated reaction rate, and the correlation coefficients are shown in FIG. 5. The correlations were done at all the studied temperatures, but only the 20° C. data is shown in FIG. 5. Reaction rate was calculated two ways (both using a linear curve fit): (1) using all the data; and (2) using 3 data points near 45 seconds.

As seen in FIG. 5, the longer the reaction proceeds, the better the correlation between absorbance and reaction rate. However, the incremental improvement for times greater than 40 seconds after $T_0$ was small. It was found that this correlation between monochloramine reaction rate and absorbance, for times>40 seconds was sufficient for correcting monochloramine interference during free chlorine measurement. Shorter times may, for example, be preferable in practice because they reduce overall method and machine time. At room temperature, the correlation coefficients obtained between the reaction rate (calculated using all data points) and absorbance was similar to the correlation coefficients obtained between the reaction rate (using three-data-point near 45 seconds) and absorbance.

Figure 6:
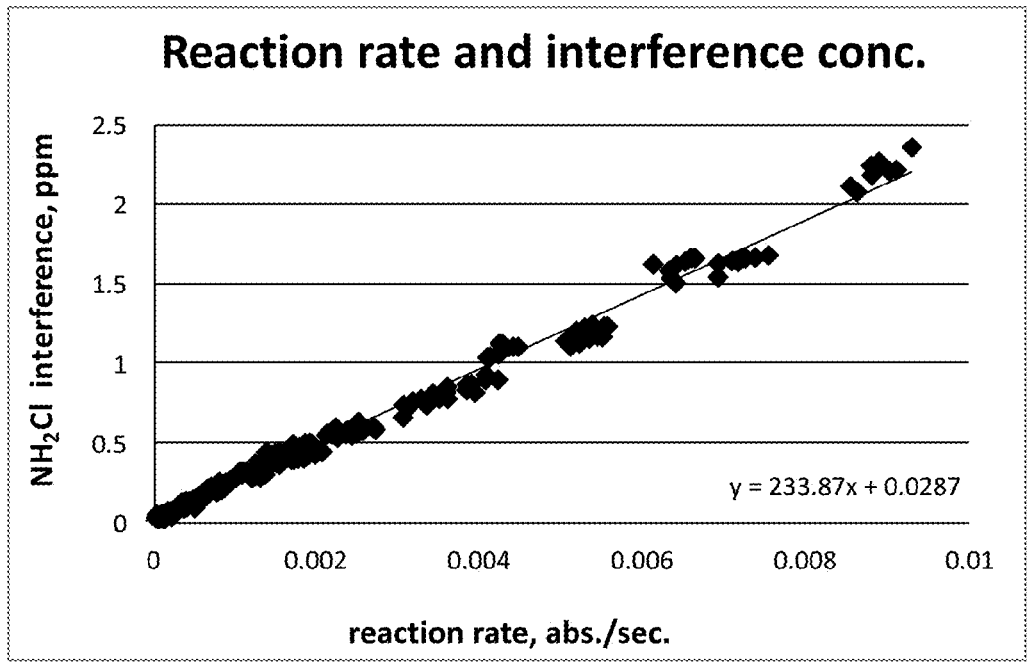
FIG. 6 illustrates monochloramine interference concentrations (ppm $NH_2Cl$ interference) versus reaction rate (change in absorbance/second), under all temperature conditions studied, wherein the reaction rate was calculated from 3 data points close to 45 seconds reaction time.

FIG. 6 illustrates a linear regression of monochloramine interference concentrations (ppm) versus overall reaction rate at all temperatures studied. The reaction rate was calculated using three points close to 45 seconds reaction time as discussed above. Thus, the reaction rate measured at 45 seconds (calculated from absorbance data) corresponds to the amount of monochloramine interference present in the sample. The amount of monochloramine determined via the measured reaction rate can be used as a calibration coefficient or correction factor when calculating free chlorine concentration. The amount of monochloramine can, for example, be subtracted from the reported free chlorine concentration (that is, amount of free chlorine+monochloramine interference concentration) to arrive at a compensated free chlorine concentration.

In a number of embodiments, free chlorine concentration is calculated by: 1) determining the presence of monochloramine using the rate and the reported free Cl concentration; 2) calculating calibration coefficients using, for example, the concentration at 45 seconds and reaction rate (as shown, for example, in FIG. 6); 3) applying the calibration coefficients to the concentration at 45 seconds to get the interference value; and 4) subtracting the interference value from the reported free Cl value to get the compensated free Cl value.

Thus, interference values are calculated from an experimentally determined equation of reaction rate vs. $NH_2Cl$ concentration and the calibration coefficients are the coefficients of that equation. In several embodiments, interference value is calculated as a*rate+b, where a and b are the calibration coefficients, see FIG. 6.

Figure 7:
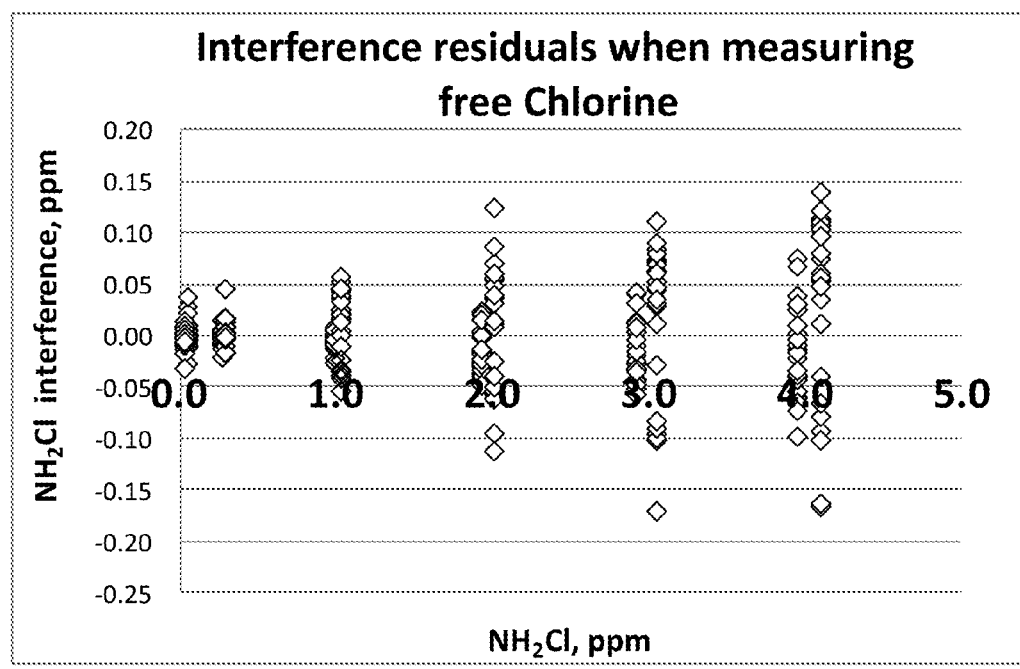
FIG. 7 illustrates monochloramine interference residuals (after applying a correction algorithm) as a function of monochloramine interference concentration (mg/L), wherein temperature varied between 5 and 50° C.

Table 8 summarizes the results for monochloramine interference in free chlorine measurement before and after the correction, at all temperatures used in the studies. FIG. 7 shows interference residuals after the monochloramine correction is applied (at all temperatures used in the studies). Ideally, the residuals should be close to zero after applying the monochloramine correction factor. In addition, the monochloramine interference values should be close to zero when there is no monochloramine in the sample.

TABLE 8

Comparison of interference reporting before and after the correction algorithm is applied.

| monoCl conc. | PPA reading, ppm | | | | | |
|---|---|---|---|---|---|---|
| | before correction | | | after correction | | |
| ppm | avg. | std. dev. | RSD, % | avg. | std. dev. | RSD, % |
| 0.03 | 0.033 | 0.004 | 111% | 0.000 | 0.012 | 1.4% |
| 0.27 | 0.095 | 0.041 | 35% | 0.002 | 0.011 | 0.8% |
| 1.00 | 0.291 | 0.160 | 29% | 0.004 | 0.025 | 0.4% |
| 1.96 | 0.559 | 0.313 | 29% | −0.005 | 0.046 | −0.2% |
| 2.98 | 0.839 | 0.468 | 28% | 0.001 | 0.061 | 0.0% |
| 4.02 | 1.114 | 0.653 | 28% | −0.002 | 0.079 | 0.0% |

The correction algorithm significantly minimizes the effect of monochloramine interference, in terms of both accuracy and precision. The poor accuracy before correction is a result of the interference reaction with DPD and the large spread in the data before correction is primarily from the temperature effect. Under the same monochloramine concentration, different temperatures will affect the reaction rate differently, thus affecting the absorbance at a certain time. The reaction rate, which can be calculated from the reaction profile, absorbance vs. time, however, is a result of many factors, including temperature and monochloramine concentration. Thus the reaction rate, especially after a pre-determined period of reaction, is a good indicator of the amount of monochloramine interference when measuring free chlorine (wherein, the free chlorine reaction is substantially complete before the time period studied).

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

The invention claimed is:

1. A system of determining a concentration of free chlorine in an aqueous solution suspected of having at least one chloramine species, comprising:
 a measuring system that measures an absorbance response over time wherein the absorbance response results from reaction of the free chlorine and the at least one chloramine species with a single reagent over time after the single reagent is added to the solution, the single reagent being reactive with the free chlorine at a first kinetic rate and reactive with the at least one chloramine species at a second kinetic rate, the first kinetic rate being different from the second kinetic rate; and
 a processor system configured to determine the concentration of the free chlorine in the solution based on a determined rate of change of the absorbance response over time;
 wherein the first kinetic rate is faster than the second kinetic rate and the processor system is configured to determine the rate of change of the absorbance during a time period wherein substantially all of the free chlorine reacted with the reagent.

2. The system of claim 1 wherein the measuring system is configured to determine a first absorbance response at a time $T_1$ after a time $T_0$, which corresponds to a time the reagent is added to the solution, and the measuring system is configured to determine at least a second absorbance response at a time $T_2$ after time $T_0$, the time $T_2$ being later than time $T_1$, and the processor system is configured to determine a concentration of free chlorine at time $T_0$ via an extrapolation, performed by the processor system, using the first absorbance response and the second absorbance response.

3. The system of claim 2 wherein the extrapolation is a linear extrapolation.

4. The system of claim 1 wherein the processor system is configured to use the rate of change of the absorbance response during the time period to determine a correction factor related to the concentration of the at least one chloramine species, and the processor system is configured to use the correction factor to determine the concentration of free chlorine.

5. The system of claim 4 wherein the correction factor corresponds to the contribution of the at least one chloramine species to the absorbance response, and the processing system is configured to determine the contribution of the at least one chloramine species to the absorbance from a model of the contribution of the at least one chloramine species to the absorbance response as a function of the rate of change of the absorbance response during the time period, wherein the processor system is configured to determine the model of the contribution and the function of the rate of change.

6. The system of claim 5 wherein the model includes the effect of one or more of temperature and reagent quantity.

7. The system of claim 6 wherein the model is a mathematical regression model providing a relationship between concentration of the at least one chloramine species and rate of change of the absorbance response.

8. The system of claim 1 wherein the measuring system comprises a spectrophotometer.

9. The system of claim 1 wherein the at least one chloramine species comprises monochloramine.

10. The system of claim 9 wherein the reagent comprises at least one of DPD (N,N-diethyl-p-phenylenediamine) and SBT (N,N'-bis(2,4-di-sulfobenzyl)tolidine tetrasodium salt).

11. The system of claim 10 wherein the reagent comprises DPD.

12. The system of claim 11 wherein the measuring system determines a first absorbance response at a time $T_1$ after a time $T_0$, which corresponds to a time the reagent is added to the aqueous solution, and the measuring system determines at least a second absorbance response at a time $T_2$ after time $T_0$, the time $T_2$ being later than time $T_1$, and the processor system is configured to determine a concentration of free chlorine at time $T_0$ via extrapolation from the first absorbance response and the at least a second absorbance response of free chlorine.

13. The system of claim 12 wherein the extrapolation is a linear extrapolation.

14. The system of claim 10 wherein the first kinetic rate is faster than the second kinetic rate and the processor system, during a time period wherein substantially all of the free chlorine reacts with the reagent, is configured to determines the rate of change of the absorbance response.

15. The system of claim 14 wherein the time period occurs before the monochloramine has substantially all reacted.

16. The system of claim 15 wherein the time period is between about 5 seconds and 2 minutes after a time $T_0$ when the reagent is added to the aqueous solution.

17. The system of claim 16 wherein the time period is between about 30 seconds and 1 minute after the time $T_0$ when the reagent is added to the aqueous solution.

18. The system of claim 15 wherein the processor system is configured to use the rate of change of the absorbance response during the time period to determine a correction factor related to the concentration of monochloramine, and the concentration of free chlorine species is determined using the correction factor.

19. The system of claim 18 wherein the correction factor corresponds to the contribution of monochloramine to the absorbance response, and the contribution of monochloramine to the absorbance response is determined by the processor system from a model of the contribution of monochloramine to the absorbance response as a function of the rate of change of the absorbance response during the time period.

20. The system of claim 19 wherein the model includes the effect of one or more of temperature and reagent quantity.

21. The system of claim 19 wherein the model is a mathematical regression model providing a relationship between concentration of monochloramine and rate of change of the absorbance response.

22. A kit comprising:
- a reagent system comprising at least one of DPD (N,N-diethyl-p-phenylenediamine) and SBT (N,N'-bis(2,4-di-sulfobenzyl)tolidine tetrasodium salt);
- a measuring system that measures an absorbance response over time resulting from reaction of free chlorine and at least one chloramine species with a single reagent over time, the single reagent being reactive with the free chlorine at a first kinetic rate and reactive with the at least one chloramine species at a second kinetic rate, the first kinetic rate being different from the second kinetic rate; and
- a processor system configured to determine the concentration of the free chlorine in the sample based on a determined rate of change of the measured absorbance response over time;
- wherein the first kinetic rate is faster than the second kinetic rate and the processor system is configured to determine the rate of change of the absorbance during a time period wherein substantially all of the free chlorine reacted with the reagent.

* * * * *